United States Patent [19]
Cutler et al.

[11] Patent Number: 6,164,244
[45] Date of Patent: Dec. 26, 2000

[54] METHOD FOR TREATING AQUATIC PESTS

[75] Inventors: Horace G. Cutler, Watkinsville, Ga.; Neil A. Belson, La Plata, Md.; Rodger Dawson, Owings, Md.; David A. Wright, Solomons, Md.

[73] Assignee: Pharmacognetics, Inc., La Plata, Md.

[21] Appl. No.: 09/272,478

[22] Filed: Mar. 19, 1999

Related U.S. Application Data

[60] Provisional application No. 60/078,677, Mar. 20, 1998.

[51] Int. Cl.$^7$ .................................................. A01K 69/00
[52] U.S. Cl. ............................................................ 119/215
[58] Field of Search ................................... 119/215, 174, 119/200, 201, 234

[56] References Cited

U.S. PATENT DOCUMENTS

| | | | |
|---|---|---|---|
| 5,068,993 | 12/1991 | Millar ........................................... | 43/4 |
| 5,128,050 | 7/1992 | Gill ........................................ | 210/755 |
| 5,192,451 | 3/1993 | Gill ........................................ | 210/755 |
| 5,334,386 | 8/1994 | Lee et al. ............................. | 424/195.1 |

OTHER PUBLICATIONS

Auyong, T.K., B.A. Westfall, and R.L. Russell, "Pharmacological Aspects of Juglone." *Toxicon*, vol. 1, pp. 235–239 (1963).

Babich, H. and A. Stern, "In Vitro Cytotoxicities of 1,4–naphthaquinone and Hydroxylated 1,4–naphthaquinones to Replicating Cells." *J. Appl. Toxicol.* vol. 13 (5): 353–358 (1993), (abstract).

Claudi, R. and G.L. Mackie, *Practical Manual for Zebra Mussel Monitoring and Control*. Lewis Publishers, Boca Raton, FL, pp. 108–109.

Clark, A.M., T.M. Jurgens and C.D. Hufford, "Antimicrobial Activity of Juglone." *Phytotherapy Research*. vol. 4(1): 11–14 (1990).

Cohen, A.N., "Panel Discussion: Prevention vs. Control of Biological Invasions." Presented at the First National Conference on Marine Bioinvasions, Jan. 24–27, 1999.

Cookson, J.T., *Bioremediation engineering: design and application*, McGraw–Hill (1995), pp. 128–131.

Didry, N., L. Dubreuil, M. Pinkas, "Activity of anthraquinonic and hapthoquinonic compounds on oral bacteria." *Pharmazie*, vol. 49(9): 681–683 (1994). (abstract).

Fisher, S.W. H. Dabrowska, D.L. Waller, L. Babcock–Jackson, and X. Zhang, "Sensitivity of Zebra Mussel (Dreissena polymorpha) Life Stages to Candidate Molluscicides." Journal of Shellfish Research, vol. 13(2): 373–377 (1994).

Fisher, S. Warwick, P. Stromberg, K.A. Bruner, and J.D. Boulet, "Molluscicidal Activity of Potassium to the Zebra Mussel, Dreissena polymorpha: Toxicity and Mode of Action." *Aquatic Toxicology*, vol. 20: 219–234 (1991).

Giver, K., "Effects of the Invasive Seaweed Sargassum muticum on Native Marine Communities in Northern Puget Sound, Washington." Presented at the First National Conference on Marine Bioinvasions, Jan. 24–27, 1999.

Great Lakes Environmental Research Laboratory (GLERL), "The Ecological Approach to the Zebra Mussel Infestation in the Great Lakes," Feb. 1994.

Great Lakes Panel on Aquatic Nuisance Species (GLPANS), "*Biological Invasions*." Aug. 1996.

Hushak, L.J., "Present and Expected Economic Costs of Zebra Mussel Damages to Water Users with Great Lakes Water Intakes." *In Sea Grant Zebra Mussel Update: A 1995 Report of Research*. Ohio Sea Grant College Program, Ohio State University, Columbus, Ohio (1996), pp. 43–44.

Nalepa, T.F. and D.W. Schloesser (eds.), Zebra Mussels: Biology, Impacts, and Control. Lewis Publishers, Boca Raton, FL, 1993, preface.

National Oceanic and Atmospheric Administration (NOAA), "NOAA Backgrounder: The Effects of Zebra mussels on the Saginaw Bay and Lake Huron Ecosystems." 1996.

New York Sea Grant (NYSG), "Zebra Mussels in North American Waterways." Internet posting.

Ohio Sea Grant, "Aquatic Nuisances: Zebra Mussels in North America." Internet posting, http://www.osc.edu/Ohi...nuisances/zm/fsO45.html, 1994.

Ollinger, K. and A. Brunmark, "Effect of Hydroxy Substituent Position on 1,4–naphthaquinone Toxicity to Rat Hepatocytes." *J. Biol. Chem.* vol. 266 (32): 21496–21503 (1991). (abstract).

University of Toledo, "Zebra Mussel Control Method Kills 'em Dead." Internet posting, http://www.icenter.uto...tl/slsht/Biology.htmlx.

U.S. Patent No. 3,602,194. U.S. Secretary of the Interior, "Method of Fish Culture." Issued Aug. 31, 1971.

U.S. Patent No. 4,178,711. Mermal, H.J., G.A. Mermal, D.J. Mermal, and R.M. Mermal, "Method for Use in Harvesting Earthworms." Issued Dec. 18, 1979.

Wilkinson, T., "Zebras Musseling In." Washington Post, p. H–1, May 14, 1997.

Wisconsin Sea Grant, "Zebra Mussels and Other Nonindigenous Species." Internet posting, http://h20.seagrant.wi...glnetwork/exotics.html.

Wright, D.A., R. Dawson, E.M. Setzler–Hamilton, "Chesapeake Bay Ballast Water: An Investigative Assessment of Excimer UV as a Method of Shipboard or Dock–Side Treatment." (unpublished, 1998).

Waller, D.L., J.J. Rach, W.E. Cupe, L.L. Marking, S.W. Fisher and H. Dabrowska, "Toxicity of Candidate Molluscicides to Zebra Mussels (Dreissena polymorphs) and Selected Nontarget Organisms." *J. Great Lakes Res.*, vol. 19(4):695–702 (1993).

*Primary Examiner*—Thomas Price
*Attorney, Agent, or Firm*—Nash and Titus, LLC

[57] ABSTRACT

A novel method for eliminating or reducing, or otherwise treating, aquatic pests using juglone or juglone analogs is described. The methods are useful for removing zebra mussels and quagga mussels from water intake pipes and various other underwater hard surfaces. In addition, the methods are useful for treating dinoflaggellates, algae and amphipods, among other pests, from ballast water. A great advantage that these methods have over current protocols is that they have low environmental risk.

34 Claims, No Drawings

METHOD FOR TREATING AQUATIC PESTS

This application claims priority from the provisional application serial No. 60/078,677, filed Mar. 20, 1998, the entire contents of which are incorporated herein by reference.

This invention was made with U.S. government support under EPA Contract No. 68D70019 awarded by the U.S. Environmental Protection Agency. The government has certain rights in the invention.

FIELD OF THE INVENTION

The invention of this application relates to novel methods for eradicating, reducing the growth of, or otherwise treating aquatic pests.

BACKGROUND OF THE INVENTION

The Problems Associated With Zebra Mussels

Accidentally introduced into the United States in the mid-1980's, zebra mussels (*Dreissena polymorpha*) have become a major threat to U.S. inland fresh water supplies. Zebra mussels have now spread throughout the Great Lakes region and as far south as Louisiana, and could cause more than $2 billion in economic damage by 1999.

Zebra mussels rapidly establish colonies on hard underwater surfaces, such as water intake pipes, boat hulls, and commercial fishing nets, forming layers up to eight inches thick (Wisconsin Sea Grant (WSG)). They can cluster together in colonies which can exceed a hundred thousand per square meter. A mature female can produce up to 40,000 eggs in one season (New York Sea Grant (NYSG)). Although a few species of fish and diving ducks eat the mussels, natural predators in North America are insufficient to control their growth.

Zebra mussels clog water intake pipes, diminishing the flow rate of water and adversely affecting industries, such as power plants, which rely on a continuous supply of intake water. Plants drawing water from infested areas have experienced 50% declines in intake efficiency (Nalepa and Schloesser, 1993). Recent studies also indicate that zebra mussels accelerate corrosion of iron and steel structures. The zebra mussel problem is particularly acute in the Great Lakes region, where about 655 billion gallons of water are withdrawn each day for use by more than 25 million people and hundreds of industries and power plants (NYSG).

Zebra mussels also significantly impact municipal drinking water supplies. In addition to clogging intake pipes, zebra mussels feed heavily on phytoplankton, dramatically increasing water clarity and promoting aggressive growth of aquatic weeds. This has led to taste and odor problems in drking water supplies. Drinking water supplies are further harmed from the putrefying flesh which occurs when zebra mussels die within intake pipes.

Zebra mussels also cause highly damaging ecological effects. Zebra mussel feeding has reduced some forms of phytoplankton, the base of the food chain, by as much as 80% (WSG). The reduction of plankton at the food chain base diminishes energy available for fish production, which is likely to reduce fish yields. The consumption of phytoplankton and related filtering of water by zebra mussels has increased water clarity in Lake Erie by up to 600% (WSG), altering the physical and chemical environment. As noted, one effect has been increased growth of aquatic weeds. Increased weed growth favors some fish species, such as sunfish, that prefer to spawn and hide in weed beds. However, wildlife biologists fear that increased water clarity will lead to the collapse of the $900 million walleye fishery, because the walleye favors turbid water (GLERL, 1994). In addition, zebra mussels have also nearly eliminated several native clam species from parts of the Great Lake region.

Zebra mussels also mobilize toxins from sediments into the food chain. Zebra mussels are capable of accumulating approximately 10 times more PCBs and other toxic contaminants than native mussels (WSG). They ingest these toxins in their fatty tissues when they eat algae to which toxins have been sorbed. When fish or birds eat these mussels, these toxic compounds then pass into the food chain in concentrated volumes.

In addition, zebra mussels help to promote growth of certain blue-green algae known as Microcystis, which are toxic to fish and cause gastrointestinal problems in humans. Zebra mussels tend to avoid Microcystis, while aggressively consuming less toxic species. This selective feeding has resulted in Microcystis blooms in Lake Erie and surrounding waters (NOAA, 1996).

Another related threat, the quagga mussel (*Dreissena bugensis*), has also recently been identified. Quagga mussels are similar to zebra mussels, but are found more than three times deeper in fresh water than zebra mussels. While zebra mussels are generally limited to shallow waters, quagga mussels pose a threat to boats and equipment located in much deeper waters.

A 1994 survey of electric generating power plants, municipal water systems and industrial water users in the Great Lakes region found that the average facility had expended over $430,000 on zebra mussel prevention and control as of 1994. Private utilities had spent an average of $869,000 per facility on control (Hushak, 1995). These amounts have undoubtedly increased substantially since 1994. The City of Baltimore has targeted $4.6 million to install zebra mussel control systems to protect its drinking water supplies, even though zebra mussels have not yet invaded Maryland (Wilkinson, 1997).

The most common treatment for zebra mussels is chlorination. Chlorine is effective against zebra mussels at low doses, and is typically applied continuously at concentrations varying between 0.5 mg/l to 2–3 mg/l (depending on time of season and whether chlorine is being applied to prevent or treat mussel infestation). However, chlorine can produce a wide variety of carcinogenic and other toxic by-products. Chlorine typically cannot be applied directly in fresh water lakes due to environmental concerns. Because of environmental problems, the Ohio Sea Grant (OSG) has stated that it no longer recommends chlorine disinfection to treat zebra mussels (OSG, 1994).

The Problems Associated With Ballast Water

An estimated 20 billion gallons of ballast water enters U.S. ports annually (Wright et al., 1998). Many major aquatic nuisances arrived in the U.S. in ballast water, including zebra mussels and other species. These non-indigenous species sometimes cause severe economic losses, damage or destroy ecosystems, and cause a loss of biodiversity. Some organisms are capable of causing death or illnesses.

The damages caused by the zebra mussels are documented above. Other exotic species have also caused serious economic and ecological damage. For instance, the shore crab, *Hemigrapsus sanguineas*, was first discovered on the U.S. Atlantic Coast in 1988 in New Jersey. It has now spread from Massachusetts to North Carolina. The exotic marine/ estuarine brown mussel has displaced native mollusks and threatens mangrove communities in the gulf of Mexico. (GLPANS, 1996).

The seaweed species *Sargassum muticum* was introduced into the U.S. West Coast in the 1940's and is now found from British Columbia to California. Its efficient dispersal methods and fast growth allow it to compete effectively with native species for space and light. It supports a very different group of organisms than native seaweed species, thus transforming entire ecosystems (Giver, 1999).

Hydrilla, an introduced plant species, has become a major pest. In Florida, the area infested by hydrilla doubled between 1994 and 1996, to 100,000 acres of inland water. The state spends $14 million annually to control this plant, which affects several other parts of the U.S. as well (GLPANS, 1996).

Several introduced species pose health risks. The Chinese mitten crab, introduced into San Francisco Bay, is host to the oriental lung fluke, a parasite affecting humans and other mammals (Id.). A South American human cholera strain was found in ballast tanks in the port of Mobile, Ala. in 1991 (Id.).

Approximately 230 exotic species are now established in the San Francisco Estuary, with approximately four new species becoming established every year (Cohen, 1999). A recent study indicated that more than 90 percent of 70 vessels surveyed in the Chesapeake Bay carried live organisms in their ballast, including barnacles, clams, mussels, microscopic plants and animals, and fish (GLPANS, 1996).

Present controls for ballast water consist largely of exchanging fresh water for salt water at sea, in order to ninimize survival of salt-intolerant species. However, this exchange is frequently incompletely performed and may be waived entirely in unfavorable conditions.

International agreements governing regulation of ballast water are presently being drafted. Juglone is an ideal candidate for treatment of ballast water, because it is inexpensive, effective against a broad range of potential aquatic nuisance species and other pest species at extremely low concentrations, and can be inexpensively treated to be rendered non-toxic prior to being discharged. (Furthermore, ocean waters are alkaline, with a normal pH of about 8.2–8.3. Since juglone rapidly biodegrades in alkaline conditions, it would quickly break down even if it did enter ocean waters).

General Background

Clark et al. (1990) reported that the black walnut was historically used in the southern U.S. to treat ringworm. They found that juglone demonstrated significant antifungal activity against certain types of fungi. Auyong et al. (1963) reported that juglone had a depressant effect on goldfish and several species of rodents.

In 1971, the U.S. Interior Department received a patent entitled "Method of Fish Culture" based on the use ofjuglone. They found that juglone killed a wide variety of undesired fish species at very low concentrations and then rapidly biodegraded so that it could be used to restock a pond with new fish species shortly thereafter (DOI, 1971, U.S. Pat. No. 3,602,194).

The U.S. Department of the Interior reported in 1970 that juglone demonstrated $LD_{50}$ results ranging from 0.027 to 0.088 ppm (parts per million) against nine fish species from seven genera. The government researchers also found that there was a very narrow range between the juglone levels which permitted complete survival and those that resulted in complete mortality (DOI, 1971).

They found that juglone biodegraded so rapidly that the pond could be safely restocked with new fish in between 10 and 60 days. They recommended a treatment level of 100 to 300 ppb ofjuglone for maximum effectiveness in clearing fish ponds. (By way of comparison, chlorine is presently used in continuous treatment of zebra mussels at levels varying between 0.5 mg/l to 2–3 mg/l.) The government researchers also found that juglone demonstrated consistent toxicity across a range of temperatures (DOI, 1971).

Another patent has been issued based on the use of a derivative from black walnut husks as a means of harvesting earthworms. The black walnut derivative is mixed with water and then applied to the soil. Application of this mixture causes earthworms to come out of the soil quickly, where they can be gathered as fishing bait. (U.S. Pat. No. 4,178,711 (1979)).

Juglone has not been used heretofore to treat infestations of zebra mussels, quagga mussels or any other aquatic pest. The standard current treatment for zebra mussels is chlorination. Chlorine is commonly applied as follows:

(a) low-level continuous chlorination at 0.5 mg/l (b) 2–3 mg/l applied continuously, 3–4 weeks following zebra mussel settlement (c) 2–3 mg/l intermittently, 2–8 hours/day during the zebra mussel reproductive season (May-Nov)

Regulatory discharge limits may affect the above amounts, e.g., maximum daily discharge of 2 hours, with concentration limitations of 0.2 mg/l for 30 days average or 0.5 mg/l on a daily basis unless dechlorination is used. Regulatory limits vary from state to state.

As noted earlier, chlorine can produce a wide variety of carcinogenic and other toxic by-products. We conducted a toxicology assay for chlorine on fathead minnows and obtained an $LD_{50}$ of 0.12 ppm. Not surprisingly, this result is indicative of strong toxicity.

Several alternatives to chlorine have been suggested. Fisher et al (1991) tested five potassium salts, KI, $K_2SO_4$, K4P2O7, KCl, and KH2PO4, and found that they had $LD_{50}$'s against zebra mussels ranging from a low of 92 mg/l to a high of 226 mg/l. Claudi and Macke (1994) reported that ozone caused approximately 50% mortality in adult zebra mussels exposed to residual ozone at levels of 2 mg/l for four days, and 100% mortality after seven days.

Some proprietary chemicals for the treatment of zebra mussels are already available. Clam-Trol, produced by Betz Chemicals, and H130 produced by Calgon Corp., are registered for use in the United States. However, both compounds are acutely toxic to fish and other aquatic organisms and are believed to be quite persistent in the environment (Claudi and Macke, 1994). Furthermore, Fisher et al (1994) found that while they were effective against larvae at less than 0.2 ug/ml, these compounds had 24 hour $LD_{50}$s against 5–8 mm adults in excess of 10 mg/l. Two chlorine compounds, Bayer 73 (Bayluscicide) and Sal I, reportedly had 24 hour $LD_{50}$'s against adults of less than 60 ug/l. Both compounds are highly toxic, however. Rotenone gave an $LD_{50}$ of 0.2 ppm against early stage zebra mussel larvae, and surprisingly was more effective against adults (Fisher et al, 1994). One other natural product, endod, derived from the soapberry plant, has also been promoted as a treatment for zebra mussels. However, endod requires at least 5–20 ppm to kill zebra mussels (University of Toledo). Some non-chemical treatments are also reportedly being developed, such as UV treatment. These treatments are reportedly still prohibitively expensive. To date, none of these existing alternative treatments seems likely to replace chlorination as the standard treatment for zebra mussels.

In addition, juglone has not been used before now to clean ballast water of aquatic pests or other non-desirable nonindigenous aquatic species. As noted above, open-sea ballast water exchange is the primary means of ballast water treatment at present. This method is insufficient in preventing infestations. Gluteraldehyde has been proposed as an alternative treatment. However, gluteraldehyde requires ship-board pumping and metering equipment. It requires concentrations of 5–150 ppm to be effective and is not feasible in many situations. Other contemplated solutions, such as filters or UV radiation are complex to use, more expensive, have also proven only partially effective, and have little effect in certain areas such as the sludge layer underlying the ballast.

SUMMARY OF THE MENTION

The inventors have discovered and reduced to practice a new method for the effective elimination, reduction and/or treatment of infestations of zebra mussels (*Dreissena polymorpha*), quagga mussels (*Dreissena bugensis*) and other aquatic nuisances, which results in the death, reduction in growth and/or disruption of infestation of these aquatic pests. This method involves the use of juglone (5-hydroxy-1,4-naphthaquinone, $C_{10}H_6O_3$), and/or its analogs, homologs and derivatives (hereinafter called "juglone or juglone analogs").

Juglone's chemical formula is as follows:

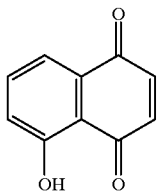

The application of juglone (and/or its analogs, homologs, and/or derivatives) effectively treats and causes broad-based mortality among zebra mussel populations at low concentrations. Juglone also biodegrades rapidly into relatively non-toxic compounds, thus minimizing environmental risks. Thus, juglone can be effective in closed-loop systems, flow-through systems, and in other water transport systems.

We have found that other compounds which effectively treat zebra mussels also treat the related aquatic nuisance, the quagga mussel. Thus, juglone can also be an effective treatment for quagga mussel infestations.

In addition to zebra mussels and quagga mussels, many other aquatic nuisances have emerged and continue to emerge. Based on the results obtained in our efficacy and toxicity trials involving juglone, we believe that juglone will also effectively treat many of these aquatic nuisances.

We also believe that juglone has anti-microbial properties, based on our results which indicate that juglone has broad biological activity. There is literature suggesting that naphthaquinones are effective against oral bacteria. We believe that juglone may prove useful in sterilizing or cleaning water in many diverse contexts. One such example is aquaculture.

Based on our results in assays for fish and zebra mussels, we also believe that juglone will be effective as an insecticide, nematicide, and for other agricultural pest control purposes. Based on the black walnut's ability to prevent other plants from growing around it, we also believe that juglone will be effective as an herbicide juglone is derived from the black walnut tree (*Juglans nigra*) and related species).

Juglone can be easily detected from its unique ultraviolet and visible spectra with a simple spectrophotometer. In particular, juglone is readily recognized from its UV-Vis spectra and can be quantified at specific wavelengths (421, 308, 250 and 209). Indeed, juglone is detectable down to about 50 ppb.

DETAILED DESCRIPTION OF THE INVENTION

Effectiveness Studies

We found that juglone applied in a 24-hour darkness test had an $LD_{50}$ against adult zebra mussels of approximately 0.36 ppm. In another 24-hour darkness test, we also found that juglone had an $LD_{100}$ against zebra mussel larvae (the stage in which zebra mussels are most vulnerable) of 0.05 ppm (or 50 ppb (parts per billion).

We also tested juglone in a 16-hour light, 8-hour darkness test against adult zebra mussels. In that test, juglone gave an $LD_{50}$ against adult zebra mussels of 2.8 ppm.

We believe that the difference in efficacy between the 24-hour darkness and the 16-hour light/8-hour darkness test is a reflection of juglone's rapid photolysis rate. Juglone, as discussed below, breaks down very rapidly in sunlight. Its breakdown rate in darkness is somewhat slower. Thus, more juglone is available for a longer time period to treat the zebra mussels in a total darkness setting. We believe that the total darkness setting approximates the conditions in many "real-life" situations where zebra mussels are clogging intake pipes and other enclosed, hard surfaces.

The results for juglone compare favorably with those for chlorine, which is the most common current treatment for zebra mussels. Chlorine's $LD_{50}$ against zebra mussel larvae is approximately 0.2 ppm, and it is typically applied in zebra mussel treatment programs at concentrations varying between 0.5 mg/l to 2–3 mg/l (depending on time of season and whether chlorine is being applied to prevent or treat mussel infestation). Chlorine also produces a wide variety of carcinogenic and other toxic by-products. Chlorine typically cannot be applied directly in fresh water lakes due to environmental concerns. Because of environmental problems, the Ohio Sea Grant has stated that it no longer recommends chlorine disinfection to treat zebra mussels (OSG, 1994).

We evaluated the effectiveness of lawsone (2-hydroxy-1,4-naphthaquinone, $C_{10}H_6O_3$) against zebra mussels and found that it had an $LD_{50}$ against zebra mussels of only approximately 58 ppm against adult zebra mussels. This is more than a 100-fold decrease in toxicity compared with juglone applied in 24-hour darkness.

The difference between juglone and lawsone is striking, given that the compounds are so similar. The primary difference between the compounds is the placement of the hydroxyl group. As is apparent from the zebra mussel tests, modification of the position of the hydroxyl group can cause a highly active compound to become relatively ineffective.

Based on these results we hypothesize that adding a hydroxyl group or other modification (particularly on the benzene ring) could possibly increase the compound's effectiveness. A review of the literature indicates that a related compound, 5,8-dihydroxy-1,4-naphthaquinone may be even more toxic than juglone (Babich and Stern, 1993; Ollinger and Brunmark, 1991). Based on these results, we believe that 5,8-dihydroxy-1,4-naphthaquinone may prove as effective or more effective than juglone. We believe that other analogs of juglone involving changed position of the hydroxyl groups or the addition of one or more hydroxyl groups may also prove active. In addition, we believe that addition of other functional groups could also enhance the activity of the compound. Examples of other analogs which may prove effective include, and are expressly not limited to, the addition of one or more bromine and/or chlorine groups. Other modifications could also enhance the activity of juglone and/or reduce its toxicity.

There are also reports in the literature that naphthaquinones, including juglone, may inhibit development of oral bacteria (Didry et al, 1994). We believe, based on our results, that juglone may have broad anti-microbial activity.

The table below summarizes our research data on the effectiveness of juglone and an analog against adult zebra mussels:

TABLE 1

Effectiveness of Juglone and its Analogs against Adult Zebra Mussels

| | $LD_{50}$ (ppm) |
|---|---|
| Juglone (24-hour darkness) | 0.36 |
| Juglone (16-hr sun/8 hr dark) | 2.6 |
| Lawsone (juglone analog) | 57.0 ppm |

TABLE 2

Effectiveness of Juglone against Zebra Mussel Larvae

| | $LD_{100}$ (ppm) |
|---|---|
| Juglone (24-hour darkness) | ≦0.05 |

Juglone was one of 18 compounds tested by Waller et al (1993) in a study of candidate molluscicides for zebra mussels. They concluded that juglone had only moderate activity, with an $LC_{50}$ of 4.3 ppm against larger (20–25 mm) adult mussels and 7.77 ppm against smaller adult (5–8 mm) mussels. They reported that the mussels tended to clamp tightly to the valves, and that there was relatively little mortality of either small adult zebra mussels or an indigenous unionid mussel species at any tested concentrations during the initial 48-hour exposure tests to juglone. Based on these results, the authors concluded that juglone did not offer commercial potential. They did not include it in a subsequent study of promising candidate treatments (Fisher et al, 1994).

We believe these authors failed to detect juglone's potent activity against zebra mussels because of their experimental design. Most importantly, the authors did not feed the adult mussels during the test. We also did not feed the mussels during our initial testing, and similarly found little mortality. Presumably, the adult mussels stopped filtering when they detected a noxious stimulus in the water. Once we introduced algae into the water as a food source, mortality rapidly ensued at low concentrations. (The use of food during the test is an accurate simulation of real-life conditions, since algae and other microorganisms on which zebra mussels feed would normally be present in intake water and on the pipes and hard surfaces where zebra mussels settle).

We also found that conducting a juglone assay in darkness dramatically increased juglone's effectiveness. We initially conducted our juglone assay using a cycle of 16 hours of light and 8 hours of darkness, and obtained an $LD_{50}$ of 2.6 ppm. However, after our photolysis study showed that juglone rapidly biodegraded in sunlight, we conducted the same assay in 24 hour darkness (similar to influent pipe conditions) and obtained an eight-fold increase in effectiveness—to 0.36 ppm.

We also found that introducing a small amount of a carrier (i.e., acetone, methanol or ethanol) significantly enhanced junglone's solubility. The Waller article does not teach any use of carriers.

Waller et al. also note that they conducted their static test in water with a pH of 7.7. We found, though, that juglone tends to destabilize in alkaline waters. Although pH 7.7 is not strongly alkaline, such a pH level could have somewhat accelerated juglone's degradation.

Finally, the authors cited junglone's toxicity to fish as a serious problem limiting its use. While we also found that juglone is toxic to fish, we found that juglone was rapidly degraded when exposed to sunlight or alkaline waters. Thus, such inexpensive treatments as liming or UV radiation should be able to minimize junglone's potential exposure to non-target organisms and the environment.

Ballast Water Studies

In addition to zebra mussels, juglone is effective against a broad range of other aquatic species. We have carried out a number of tests which demonstrate junglone's effectiveness against a broad range of aquatic species, some of which are major potential aquatic nuisances. Together with its biodegradability, these studies demonstrate its potential value as a ballast water treatment.

We also found that juglone is effective against dinoflaggellates. It was shown to inhibit growth and cell division of dinoflagellates *Prorocentrum minimum* at concentrations of 0.1 ppm. It destroys dinoflagellates at concentrations at or below 0.5 ppm. Dinoflaggellates are a problematic marine organism which cause highly toxic red tides and annually cause thousands of deaths worldwide and many more cases of sub-lethal poisoning. They are often transported in ballast water and are considered difficult to destroy because of their ability to form cysts. The toxic dinoflagellate *Prorocentrum minimum*, obtained from the Woods Hole culture collection, was cultured to exponential growth phase in F\2 media at 15 parts per thousand salinity in a 12 hour daylight, 12 hour darkness regime. A range of concentrations of juglone in acetone ranging from 50 to 1000 parts per billion were added to 10 ml sub-samples of the culture, to which were added aliquots of juglone in acetone. Cell counts using binocular microscope and hemocytometer were performed daily. In vivo chlorophyll fluorescence and motility were likewise monitored daily. Juglone's ability to destroy dinoflaggellates is a highly valuable attribute of a ballast water treatment.

We have also found that juglone is an effective algacide. It effectively controlled *Chlorella vulgaris* an estuarine green alga at concentrations below 0.1 ppm. The chlorella was cultured to exponential growth phase in F\2 media at 15 parts per thousand salinity in a 12 hour daylight, 12 hour darkness regime. A range of concentrations of juglone in ethanol were added to 400 ml sub-samples of the culture, to which were added aliquots of juglone in ethanol. Cell counts using binocular microscope and hemocytometer were performed daily. In vivo chlorophyll fluorescence was likewise monitored daily. Since a number of exotic algal species have become major pests in U.S. waters, junglone's effectiveness against algae is also a highly positive attribute in a ballast water treatment.

We carried out a 96-hour toxicology assay of juglone against fathead minnows, age 1–14 days, with a 24-hour age range. We used 10 organisms per container, with 3 replicates per concentration. We utilized 5 test concentrations plus controls. Juglone demonstrated an $LD_{50}$ in our fathead minnow assay of 0.02 ppm (20 ppb). This result is consistent with the DOI results on nine fish species reported above.

We believe that juglone is also effective in treating the organisms which inhabit the sludge at the bottom of most ship ballasts. In particular, juglone applied in sludge/sediment demonstrated an $LD_{50}$ against the amphipod *Leptocheirus plumulosis* at 1 ppm, and an $LD_{25}$ at 500 ppb. This sludge is inaccessible to many contemplated ballast water treatments (such as UV radiation). However, juglone partitions favorably from water into soils (see the octanol-water partition data below).

In addition, juglone may be effective in minimizing microbial introductions through ballast water.

Environmental Fate Analyses

Juglone has a number of environmentally-related characteristics which make it highly attractive as a new zebra mussel control agent and for other uses. Juglone biodegrades very rapidly in alkaline conditions or in response to UV radiation. It also breaks down rapidly in pond water (i.e., microbial degradation). In addition, juglone has a favorable octanol-water coefficient, which indicates little risk of storage in lipid tissues or environmental magnification. Juglone's breakdown products are relatively non-toxic materials. We believe that a primary breakdown product ofjuglone is 1,4,5-trihydroxynaphthalene. The breakdown pathways of naphthaquinones are well studied, and the primary breakdown products have been shown in the context of bioremediation to break down further into more polar compounds (Cookson, 1995).

We conducted an aquatic hydrolysis test ofjuglone at three pH values: pH 4, pH 6.8 and pH 9. The tests were conducted in 24-hour darkness.

Juglone had a half-life of only 15.4 hours in water at pH 9. The juglone virtually disappeared within 5 days. By contrast, there was minimal biodegradation (10% or less) within 12 days at both pH 6.8 and pH 4.0. (The test will continue for 30 days with respect to the samples at neutral and acid pH samples).

Juglone also showed rapid biodegradation in response to UV radiation in our preliminary photolysis test (exposure to sunlight). A 10 ppm aqueous solution of juglone was irradiated for an estimated six hours of winter sunlight conditions in a 500 ml quartz vessel. Samples were analyzed prior to and after this period of irradiation. The results demonstrated a rapid disappearance of the juglone peak on the HPLC chromatogram and an appearance of a small amount of a more polar compound. Further illumination with visible light (window with diffuse light) for a period of two days resulted in an almost complete disappearance of the juglone.

The photolysis study by its nature is a preliminary test, since the solar insulation levels were arbitrarily chosen. Juglone's rapid disappearance does indicate, however, that it breaks down rapidly in the presence of sunlight.

We also carried out a study of the combined effects of hydrolysis and aerobic microbial degradation of juglone. Triplicate samples of 100 ppm concentration of juglone were added to glass fiber-filtered freshwater pond water from a local Maryland source, with pH approximately 6.8. We utilized pond water rather than deep well water since the nutrient levels and microbial populations better represent typical environmental receiving water and thus a typical exposure route. The fortified water samples were stored at 20° C. in the dark and aerated daily. (Continuous aeration was avoided to reduce evaporation and possible volatilization).

Juglone demonstrated a half-life of only 3.6 days in pond water conditions. The juglone virtually disappeared after 18 days.

We found that juglone has an octanol-water coefficient of 96 (log $K_{ow}$ <2). We based this result on tests carried out on three different mixtures of octanol and water. This octanol-water coefficient value indicates that juglone is not likely to be stored in lipid tissues and poses little risk of magnification (i.e., concentration) in the food chain, bioaccumulation, or adsorption to sediment.

Our results strongly suggest that juglone can be inexpensively treated and broken down into non-toxic forms. Means of accelerating this breakdown include application of either lime, treatment with UV radiation (combining UV radiation with peroxide should increase breakdown further), and other related means. These treatment means are all substantially less expensive to construct and maintain than the chlorination and dechlorination facilities presently required when chlorine is used for zebra mussel control. Other related treatments should also expedite breakdown of juglone.

In order to maximize its effectiveness, juglone should be used with a solvent to enhance its water solubility. Any solvent that renders the juglone soluble in water should be sufficient for the practice of the methods of this invention, although preferably the solvent is an organic solvent. For instance, a 2.5% solution of juglone in acetone provides excellent solubility. Methanol, ethanol, isopranol, other alcohol and aromatic solvents, and other materials can also be used to enhance junglone's solubility in water.

An alternative means to increase junglone's solubility is to replace the hydrogen ion of junglone's hydroxy group with various substituted ions. Substitution of the hydrogen ion of the hydroxy group with a sodium ion provides excellent solubility, and should not affect the compounds efficacy. In water, the sodium ion will detach and the compound will flnction as juglone. This structure is as follows:

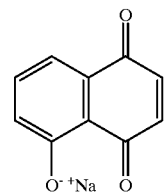

Alternatively, substitution with an amine group should also similarly provide excellent solubility without affecting efficacy. Such a structure would be as follows:

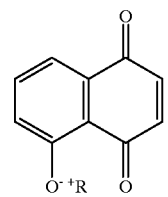

R = Primary & Secondary Amines

Several other derivative compounds could also increase juglone's solubility. The derivative compounds should be relatively simple to apply to a target site (for zebra mussel control, ballast water treatment or other use). One means of application is to place the juglone derivative into a plastic bag, along with a drying agent. Then this plastic bag may be placed directly into the ship ballast, intake pipe or other target area. The compound will gradually diffuse out of the plastic into the surrounding waters.

We also believe certain other preparations could enhance junglone's effectiveness. For example, pelletizing juglone or encapsulating it so that it has slow release could increase its effectiveness or reduce the amount of raw material needed to provide effective zebra mussel control. Other preparations could also increase its effectiveness, reduce the amount of chemical needed for effective treatment or otherwise reduce costs, and/or reduce adverse effects.

Juglone (including its analogs, homologs and/or derivatives) offers several significant advantages over existing treatments for zebra mussel infestations, treatment of ballast water, and other aquatic nuisances.

1) It is very effective at low concentrations against zebra mussels and a variety of other potential aquatic nuisance species.

a) Juglone's $LD_{50}$ against adult zebra mussels is 0.36 ppm. It has an $LD_{100}$ of 0.05 ppm against zebra mussel larvae. This is several times lower than the effective concentration of chlorine and other common zebra mussel controls.

b) Juglone effectively treats dinoflaggellates. It strongly inhibits growth of *Prorocentrum minimum* dinoflaggellates at concentrations of 0.1 ppm and effectively destroys them at or below concentrations of 0.5 ppm.

Dinoflaggellates are a problematic marine organism which cause highly toxic red tides. They are often transported in ballast water and are considered difficult to destroy because of their ability to form cysts.

c) Juglone is an effective algacide. It effectively controls Chlorella seaweed species at concentrations below 0.1 ppm.

d) Juglone is also effective in treating the organisms which inhabit the sludge at the bottom of most ship ballasts, demonstrating an $LD_{50}$ against the amphipod *Leptocheirus plumulosis* at 1 ppm, and an $LD_{25}$ at 500 ppb.

2) Juglone biodegrades rapidly, into relatively non-toxic compounds. It also poses little risk of bioaccumulation or magnification in the environment or food chain. Juglone's breakdown can be accelerated through such simple mechanisms as UV treatment or liming. Because juglone rapidly biodegrades under alkaline conditions, it is ideal for ballast water treatment. Ocean water has a pH of approximately 8.2. Thus, juglone would rapidly biodegrade if discharged in ocean water. Because of its biodegradability, juglone offers significant advantages over chlorine and other highly toxic existing chemical treatments for zebra mussels and other aquatic nuisances which pose significant environmental hazards.

3) Because of its lower environmental risks, juglone may be suitable for use in many situations where existing chemical treatments are not suitable for environmental reasons.

4) Juglone is inexpensive and relatively simple to use. It can be applied effectively with a solvent such as acetone. Alternatively, a sodium, amine or other derivative can be manually applied directly into the target location, and the juglone will then diffuse throughout the target site. Because it breaks down rapidly, it does not require construction of expensive chlorination and dechlorination (or related) facilities. As noted above, biodegradation of juglone can be accelerated through such inexpensive mechanisms as UV treatment or liming.

5) Juglone is inexpensive to produce. It can be isolated from walnut husks of *J. nigra, J. cinerea, J. regia* or Juglandaceae or it can be synthesized by oxidation of 1,5-dihydroxynaphthalene. Extraction of juglone from walnut husks may be accomplished by leaching with ether or other solvents. Purification of the crude extract may be accomplished in a variety of conventional ways including sublimation (DOI, 1971).

REFERENCES

Auyong, T. K., B. A. Westfall, and R. L. Russell, "Pharmacological Aspects of Juglone." *Toxicon*, Vol. 1, 235–239 (1963).

Babich, H. and A. Stem, "In Vitro Cytotoxicities of 1,4-naphthaquinone and Hydroxylated 1,4-naphthaquinones to Replicating Cells." J. Appl. Toxicol. 13 (5): 353–358 (1993).

Claudi, R. and Mackie, G. L., *Practical Manual for Zebra Mussel Monitoring and Control*. Lewis Publishers, Boca Raton, Fla., pp. 108–109.

Clark, A. M., T. M. Jurgens, and C. D. Hufford, "Antimicrobial Activity of Juglone." *Phytotherapy Research*, Vol. 4(1), 11–14 (1990).

Cohen, A. N., "Panel Discussion: Prevention vs. Control of Biological Invasions." Presented at the First National Conference on Marine Bioinvasions, Jan. 24–27, 1999.

Cookson, J. T., *Bioremediation engineering: design and application*, pp. 128–131. McGraw-Hill (1995).

Didry, N., L. Dubreuil, M. Pinkas, "Activity of anthraquinonic and hapthoquinonic compounds on oral bacteria." *Pharmazie* 49(9): 681–683 (1994).

Fisher, S. W., Dabrowska, H., Waller, D. L., Babcock-Jackson, L. and Zhang, X., "Sensitivity of Zebra Mussel (*Dreissena polymorpha*) Life Stages to Candidate Molluscicides." *Journal of Shellfish Research*, Vol.13 (2): 373–377, 1994.

Fisher, S. Warwick, Stromberg, P., Bruner, K. A., and Boulet, J. D., "Molluscicidal Activity of Potassium to the Zebra Mussel, *Dreissena polymorpha*: Toxicity and Mode of Action. *Aquatic Toxicology* 20: 219–234, 1991.

Giver, K., "Effects of the Invasive Seaweed *Sargassum muticum* on Native Marine Communities in Northern Puget Sound, Wash. Presented at the First National Conference on Marine Bioinvasions, Jan. 24–27, 1999.

Great Lakes Environmental Research Laboratory (GLERL), "The Ecological Approach to the Zebra Mussel Infestation in the Great Lakes," February 1994.

Great Lakes Panel on Aquatic Nuisance Species (GLPANS), "*Biological Invasions*," August, 1996.

Hushak, L. J., "Present and Expected Economic Costs of Zebra Mussel Damages to Water Users with Great Lakes Water Intakes." In *Sea Grant Zebra Mussel Update: A 1995 Report of Research*. Ohio Sea Grant College Program, Ohio State University, Columbus, Ohio, 1996, pp. 43–44.

Nalepa, T. F. and Schloesser, D. W. (eds), *Zebra Mussels: Biology. Impacts. and Control*. Lewis Publishers, Boca Raton, Fla., 1993, preface.

National Oceanic and Atmospheric Administration (NOAA), "NOAA Backgrounder: The Effects of Zebra Mussels on the Saginaw Bay and Lake Huron Ecosystems," 1996.

New York Sea Grant (NYSG), "Zebra Mussels in North American Waterways," internet posting.

Ohio Sea Grant, "Aquatic Nuisances: Zebra Mussels in North America." Internet posting, http://www.osc.edu/Ohi... nuisances/zm/fs045.html, 1994.

Ollinger, K. and A. Brunmark, "Effect of Hydroxy Substituent Position on 1,4-naphthaquinone Toxicity to Rat Hepatocytes." J. Biol. Chem. 266 (32): 21496–21503 (1991).

University of Toledo, "Zebra Mussel Control Method Kills'em Dead." Internet posting, http://www.icenter.uto...tl/slsht/Biology.htmlx.

U.S. Pat. No. 3,602,194. U.S. Secretary of the Interior (DOI), "Method of Fish Culture." Issued Aug. 31, 1971.

U.S. Pat. No. 4,178,711. Mermal, H. J., G. A. Mermal, D. J. Mermal, and R. M. Mermal, "Method for Use in Harvesting Earthworms." Issued Dec. 18, 1979.

Wailer et al., "Toxicity of Candidate Molluscicides to Zebra Mussels (*Dreissena polymorpha*) and Selected Non-target Organisms", J. Great Lakes Res., 19(4):695–702, Internat. Assoc. Great Lakes Res., 1993.

Wilkinson, T., "Zebras Musseling In." Washington Post, p. H-1, May 14, 1997.

Wisconsin Sea Grant (WSG), "Zebra Mussels and Other Nonindigenous Species." Internet posting, http://h20.seagrant.wi...glnetwork/exotics.html.

Wright, D. A., Dawson, R., Setzler, Hamilton, E. M., "Chesapeake Bay Ballast Water: An Investigative Assessment of Excimer UV as a Method of Shipboard or Dock-Side Treatment." (unpublished, 1998).

All of the above-mentioned references are entirely incorporated herein by reference.

What is claimed is:

1. A method for treating infestations of aquatic pests with minimal environmental risks, comprising the steps of:
   (a) exposing aquatic pests to an effective amount of a composition comprising juglone or a juglone analog and an organic solvent, and
   (b) allowing the juglone or juglone analog to biodegrade.

2. The method of claim 1, wherein the aquatic pests are selected from the group consisting of zebra mussels, quagga mussels, dinoflaggellates, amphipods, and algae.

3. The method of claim 1, wherein the aquatic pests are zebra mussels.

4. The method of claim 3, wherein the effective amount of the composition includes at least 50 ppb of juglone.

5. The method of claim 1, wherein the infestations are present in or on intake water pipes, boat hulls, underwater hard surfaces, and fishing nets.

6. The method of claim 1, wherein the solvent is selected from the group consisting of acetone, isopropanol, methanol, ethanol, and mixtures thereof.

7. The method of claim 1, wherein the solvent is acetone.

8. The method of claim 7, wherein the juglone or juglone analog is present in a concentration of 2.5% in acetone.

9. The method of claim 1, wherein the juglone or juglone analog biodegrades in alkaline conditions.

10. The method of claim 9, wherein lime is added to facilitate biodegradation of the juglone or juglone analog.

11. The method of claim 1, wherein the juglone or juglone analog biodegrades in sunlight or ultraviolet radiation.

12. The method of claim 1, wherein the juglone or juglone analog biodegrades in the presence of microorganisms.

13. The method of claim 1, wherein the aquatic pest is exposed to the composition in the presence of a food source.

14. The method of claim 1, wherein the juglone or juglone analog is obtained by extraction of walnut husks or is synthesized.

15. The method of claim 14, wherein the juglone or juglone analog is obtained by extraction of walnut husks or is synthesized.

16. The method of claim 1, wherein aquatic pests are killed.

17. The method of claim 16, wherein growth of aquatic pests is reduced.

18. The method of claim 16, werein infestation of aquatic pests is disrupted.

19. A method for eliminating or reducing aquatic pests in ballast water with minimal environmental risks, comprising the steps of:
   (c) exposing aquatic pests in ballast water to an effective amount of a composition comprising juglone or a juglone analog and an organic solvent, and
   (d) allowing the juglone or juglone analog to biodegrade.

20. The method of claim 19, wherein the aquatic pests are selected from the group consisting of zebra mussels, quagga mussels, dinoflaggelates, amphipods, and algae.

21. The method of claim 19, wherein the aquatic pests are zebra mussels.

22. The method of claim 21, wherein the effective amount of the composition includes at least 50 ppb of juglone.

23. The method of claim 19, wherein the solvent is selected from the group consisting of acetone, isopropanol, methanol, ethanol, and mixtures thereof.

24. The method of claim 19, wherein the solvent is acetone.

25. The method of claim 24, wherein the juglone or juglone analog is present in a concentration of 2.5% in acetone.

26. The method of claim 19, wherein the juglone or juglone analog biodegrades in alkaline conditions.

27. The method of claim 26, wherein lime is added to facilitate biodegradation of the juglone or juglone analog.

28. The method of claim 19, wherein the juglone or juglone analog biodegrades in sunlight or ultraviolet radiation.

29. The method of claim 19, wherein the biodegradation of the juglone or juglone analog is effected by discharging the ballast water into the ocean.

30. The method of claim 19, wherein the juglone or juglone analog biodegrades in the presence of microorganisms.

31. The method of claim 19, wherein the aquatic pest is exposed to the composition in the presence of a food source.

32. The method of claim 19, wherein aquatic pests are killed.

33. The method of claim 19, wherein growth of aquatic pests is reduced.

34. The method of claim 19, wherein infestation of aquatic pests is disrupted.

* * * * *